(12) United States Patent
Skog et al.

(10) Patent No.: US 6,295,330 B1
(45) Date of Patent: Sep. 25, 2001

(54) DEVICE FOR REPEATED REGISTRATION OF THE NUMBER OF THERMAL CYCLES TO WHICH A PART FOR MEDICAL USAGE HAS BEEN SUBJECTED

(75) Inventors: Göran Skog, Bromma (SE); Erik Krahbichler, Straubing (DE); Bruno Slettenmark, Järfälla (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/365,899

(22) Filed: Aug. 3, 1999

(30) Foreign Application Priority Data

Aug. 5, 1998 (SE) .................................. 9802674

(51) Int. Cl.$^7$ ........................................ G07C 3/00
(52) U.S. Cl. .................................. 377/15; 377/16
(58) Field of Search ............................ 377/16, 15

(56) References Cited

U.S. PATENT DOCUMENTS

| | | | |
|---|---|---|---|
| 4,449,518 | 5/1984 | Konomura et al. | 128/4 |
| 5,313,935 | 5/1994 | Kortenbach et al. | 128/4 |
| 5,359,993 | 11/1994 | Slater et al. | 128/4 |
| 5,383,874 | 1/1995 | Jackson et al. | 606/1 |
| 5,400,267 | 3/1995 | Denen et al. | 364/552 |
| 5,452,335 | 9/1995 | Slater et al. | 377/25 |
| 5,991,355 | * 11/1999 | Dahlke | 377/15 |

FOREIGN PATENT DOCUMENTS

| | | |
|---|---|---|
| 198 25 754 | 1/1999 | (DE) . |
| 0 581 400 | 2/1994 | (EP) . |
| 1 252 034 | 11/1971 | (GB) . |

* cited by examiner

Primary Examiner—Margaret R. Wambach
(74) Attorney, Agent, or Firm—Schiff Hardin & Waite

(57) ABSTRACT

A device for repeated registration of the number of thermal cycles to which a part for medical usage has been subjected has a temperature-sensitive element and/or a pressure-sensitive element arranged in conjunction with the part. This element reversibly changes its physical shape with temperature and/or pressure, variations in pressure being invariably associated with changes in temperature. A registration unit registers this change in shape when it exceeds a specific threshold value, as an indication of the part undergoing, or having undergone, a thermal cycle.

35 Claims, 7 Drawing Sheets

DEVICE FOR REPEATED REGISTRATION OF THE NUMBER OF THERMAL CYCLES TO WHICH A PART FOR MEDICAL USAGE HAS BEEN SUBJECTED

BACKGROUND OF THE INVENTION

1. Field of the Invention

The present invention relates to a device for repeated registration of the number of thermal cycles to which a part for medical usage has been subjected.

2. Description of the Prior Art

A large number of parts or components in medical devices require sterilization between each use. This is often accomplished by heating the part or component in an autoclave. For safety reasons, these parts or components may not be reused more than a limited number of times. Therefore, careful monitoring and reliable, tamper-proof checking of the number of times parts and components are reused are very important. The number of times a part has been autoclaved has hitherto often been determined by using a logbook, a technique which can vary as to reliability.

U.S. Pat. No. 5,383,874 describes a system for identifying and monitoring the use of ablation catheters. This system employs a usage register, whose contents are incremented by one every time the catheter is put to authorized use, to ensure that the catheter is not used too frequently.

German 05 19825 754 (corresponding to co-pending U.S. application Ser. No. 09/098,495 filed Jun. 17, 1998) describes a device for counting the number of usage cycles by a sensor for intracorporeal electrophysiological measurement and/or therapy. Here, a counter connected to the sensor contains an identification code specific to the sensor, and connection! disconnection of the sensor to/from external measurement equipment and/or therapeutic equipment is detected. The identification code is used for determining, from information stored in a main computer on previous usage, whether conditions for a new usage cycle have been met and, if so, incrementing counter contents by one usage cycle.

Another system for counting usage cycles is disclosed in U.S. Pat. No. 5,400,267.

Disinfecting indicators are also known, as described in U.S. Pat. No. 4,449,518 which discloses such an indicator using a memory alloy. The indicator is deformed when the device is used and re-assumes its shape when exposed to heat. This system does not register the number of disinfecting or heat cycles.

U.S. Pat. Nos. 5,313,935; 5,359,993; and 5,452,335 and European Application 581 400 all essentially show devices for indicating the number of thermal cycles by moving a cog wheel one step for each cycle. On the cogs, indicator numbers are placed. Through a window of the indicator numbers can be viewed, indicating a present number of thermal cycles. However, none of these devices can indicate whether the device has gone through a thermal cycle before a new use of the device. Since the indicator numbers are placed on the cogwheels, the total number of thermal cycles is limited to fairly low numbers. This because the indicator numbers must be significantly large for a user to read.

The ability to distinguished sterilized replaceable items from unsterilized items is also of the greatest importance in this field. At present, unsterilized and sterilized components are usually stored at different locations, but mix-ups may occur because the appearance of an item does not indicate whether the item has been sterilized.

SUMMARY OF THE INVENTION

An object of the present invention is to resolve the aforementioned problems associated with prior art devices and to supply the part or component for medical usage with an indicator showing the user not only the number of uses/thermal cycles but also whether the part or component has completed the prescribed thermal cycle after its most recent use.

Another object of the present invention is to provide a device for repeated usage/thermal cycle registration, where the number of cycles is almost unlimited.

The above object is achieved in accordance with the principles of the present invention in a device for repeated registration of the number of thermal cycles to which a part for medical usage is subjected, wherein a temperature-sensitive element and/or a pressure-sensitive element is arranged in conjunction with the part, the element (or elements) reversibly changing in physical shape with temperature and/or pressure (variations in pressure always occurring with changes in temperature), and wherein an indicator element is arranged to move from a first indication position to a second indication position when the aforementioned change in shape exceeds a predetermined threshold value, and wherein a registration unit identifies movement of the indicator element from the first indication position the second indication position, thereby registering the fact that the part has undergone a thermal cycle.

By using a temperature-sensitive element and/or pressure-sensitive element, whose physical shapes changes in a reversible fashion with changes in temperature and/or pressure (variations in pressure always occurring with changes in temperature), attached to the part or component, any change in shape can be utilized for moving an indicator element from a first indication position to a second indication position, thereby providing e.g. a visual indication of whether the part or component has completed the thermal cycle. The risk of non-autoclaved parts being put to use is thus eliminated. The movements of the indicator element can be registered by a registration unit. Thus, the invention is based on movements of an indicator element from a first indication position to a second indication position a large number of times.

The relevant thermal cycle is not limited to autoclaving but could also be e.g. washing in hot water.

In an embodiment of the device according to the invention, a reset arrangement automatically resets the indicator element to a first indication position upon the occurrence of a predetermined condition, such as when the part for medical usage is put to use or is attached to a mother unit. When the mother unit is a ventilator and the part for medical use is an expiration line cassette, the reset arrangement can reset the indicator element to the first indication position when an expiratory valve opens a first time. Alternatively, the indicator element can be reset with e.g. a small pulse magnet, motor or the like.

In another embodiment of the device according to the invention, the indicator element is a plate with two differently colored fields, this plate being moveable in a window to display one of the fields in the first indication position and the other field in the second indication position. In addition to direct visual observation of the plate's position, the position of the plate also can be detected e.g. with an optical detector. Alternatively, the plate can control a mechanical switch for opening and closing an electric circuit, or the plate's movement can be detected with an inductive or capacitive sensor.

In a further embodiment of the device according to the invention, a memory accumulatively stores the total number (running total) of registered shape changes made by the temperature-sensitive element and/or pressure-sensitive element. The memory can be arranged in the part for medical usage, in a separate reader unit or in a mother unit in which the part for medical usage is intended for use. In this manner, the total number of thermal cycles completed by the part for medical usage can be reliably counted.

According to another embodiment of the device of the invention, the part for medical usage is assigned a specific identification code, and the reader unit or the mother unit contains a sensor unit for sensing that code and incrementing the number of shape changes registered for the identified part by one when the part for medical usage is connected to the reader unit or mother unit after completing a thermal cycle. This makes it possible to count the total number of thermal cycles completed by the part for medical usage, even in instances in which the part is used in different mother units. This is particularly advantageous in environments using computer networks and databases for controlling, monitoring and/or supervising medical equipment.

In another embodiment of the device according to the invention, the indicator element is adapted to perform accumulating, one-way movement, with the second indication position in one thermal cycle corresponding to the first indicator position in a following thermal cycle. In this manner, registration is linked to the part for medical usage and the number of registered changes in shape, i.e. the number of completed thermal cycles, can be easily read, e.g. visually on a graded scale. No special sources of energy, batteries, active electronic components, chemicals etc. are required, and a simple, sturdy, reliable, encapsulated, relatively small and inexpensive device is achieved.

In another embodiment of the device according to the invention, the registration unit is a tube whose interior surface is provided with notches along the length of the tube. Inside the tube, the temperature-sensitive element and/or pressure-sensitive element and indicator element are coupled together to form a moving body which reversibly changes its length with the temperature, this body having a set of wings or flanges which mesh with the notches in the wall of the tube, forming a ratchet pawl, so the moving body performs an accumulating movement along the tube only when its change in length during a thermal cycle exceeds the distance between two consecutive notches. In this manner, the moving body only "advances" when its change in length is greater than or equal to the distance between two consecutive notches. This prevents any "advancing" caused by normal thermal expansion of the body without the body completing the prescribed thermal cycle in which a specific threshold temperature $T_1$ is exceeded. This also eliminates the risk of the body being intentionally shifted or moved in the wrong direction in some other way. The device's reliability is accordingly enhanced in this embodiment.

In a further embodiment of the device according to the invention, the registration unit is a tube and the moving body is a threaded rod arranged inside the tube and two threaded wheels, equipped with ratchet pawl wings pressing on the interior wall of the tube and installed with a gap between them, and the threaded wheels are connected to the temperature-sensitive element and/or pressure-sensitive element, whose shape changes in a jump when the temperature exceeds a threshold value, causing the wheels to rotate one-way and advance along the threaded rod in steps every time the temperature cycle exceeds a temperature threshold. The interior of the tube has notches at specific distances around the circumference. In this embodiment, a helical movement is employed, making the device more reliable, more accurate and less sensitive to jolts, acceleration and vibration than is the case with linear movement. Moreover, a far greater number of thermal cycles can be registered for any given device size. Providing the interior of the tube with notches also increases reliability analogously to the method employed in the aforementioned embodiment with linear movement by the registering body.

When the interior of the tube is smooth, "resolution" is infinitely great in theory but finite in practice due to friction, the resiliency of the wings etc. If expansion is very slight, the moving body will not "advance" but remain in place and quiver.

In another embodiment of the device according to the invention, the number of notches around the circumference of the tube's interior wall and the number of ratchet wings differ. High resolution accordingly can be achieved with a few wings and notches, thereby facilitating fabrication.

In another embodiment of the device according to the invention, the temperature-sensitive element and/or pressure-sensitive element is made of memory metal. Such an element reversibly changes its physical shape at a specific "switching temperature" that can be selected within wide limits. The change in shape as well as the mechanical force developed can be made large. In this way, a distinct change in shape can be achieved when the switching temperature is exceeded. This change in shape can be used for registering the thermal cycle. The switching temperature and elongation of the body when this temperature is reached can be set with a tempering and deformation procedure at the time the body is manufactured. The memory metal's change in shape when the switching temperature is reached is of a different order of magnitude than conventional, linear, thermal expansion. Since a body made of memory metal can develop considerable force, friction between the body and the wall of the tube can be made relatively large to keep jolts, vibration, forces of acceleration etc. from moving the body inside the tube.

In a further embodiment of the device according to the invention, the temperature-sensitive element and/or pressure-sensitive element is a bimetallic element. A bimetallic element can produce a large change in shape, which, however, is linear with the temperature. The bimetallic element is devised so its linear elongation with the temperature is equal to the distance between two consecutive notches at a pre-selected temperature threshold which is exceeded at some point in the thermal cycle in question. The moving body will then advance one step for every cycle in which the temperature exceeds this threshold.

In another embodiment of the device according to the invention, the thermal cycle entails autoclaving under positive pressure, i.e. steam autoclaving. The moving body then is a hermetically sealed bellows arranged to be compressed by the positive pressure. Elongation of the bellows after autoclaving produces the body's movement in the tube. As a result of the positive pressure, considerable compressive force develops, and a desired elongation of the bellows in an autoclaving cycle can be achieved through an appropriate choice of bellows stiffness.

In another embodiment of the device according to the invention, the tube is transparent. The position of the moving body, designating the number of thermal cycles completed, can be conveniently read from e.g. a scale, as with a conventional thermometer.

In a further embodiment of the device according to the invention, the moving body, or a device or an appliance attached to the moving body, is arranged to act successively on a component with variable resistance and/or inductance and/or capacitance related to the body's movement. In this manner, electronic reading and display of the number of thermal cycles completed is achieved, preferably in the mother apparatus since the part for medical usage should be relatively simple and inexpensive and is also exposed to moisture, high temperatures etc. In the device according to the invention, a coil is wound around the tube in turns which increase linearly from one end of the coil to the other, and a small part of ferromagnetic, non-magnetized material can be attached to the moving body so it moves successively inside the coil when the body moves. This coil can be arranged in the mother apparatus. The coil accordingly can encircle the tube when the part for medical usage is mounted on the mother apparatus.

In the last mentioned embodiment, a commercially available standard component, such as a component whose resistance and/or inductance and/or capacitance changes with the body's movement, can naturally be used.

In another embodiment of the device according to the invention light variation-sensitive receptor is arranged to register light transmitted from a light source across the tube, and the moving body tapers at one end, or is connected to an appliance with a tapered end, so the body's movement gradually shadows the flow of light. In this version, the light receptor can be mounted on the tube or be located in the mother apparatus.

In another embodiment of the device according to the invention, two separate wheels, which only rotate in one direction, are arranged on a rod, the wheels being interconnected to the temperature-sensitive element and/or pressure-sensitive element which is devised so the wheels rotate in steps through specific accumulating angle each time a thermal cycle exceeds a temperature threshold. In this embodiment, the accumulated angular rotation of the wheels designates the number of completed thermal cycles. This rotary movement can be used to e.g. move a piece of iron inside a coil so rotation changes inductance, rotate a potentiometer shaft to change resistance, move a cone in an optical path in order to shadow transmitted light or rotate a variable capacitor or a variable inductor etc. in order to achieve a measurable parameter that varies with rotation. Commercially available electrical components can be used.

DESCRIPTION OF THE PREFERRED EMBODIMENTS

Figure 1:
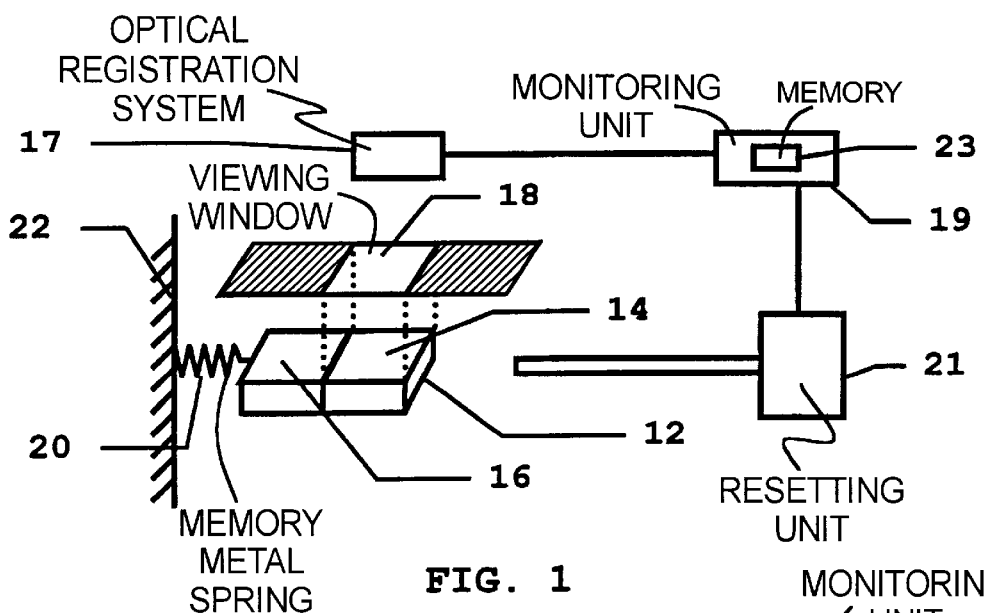
FIGS. 1–3 illustrate the structure and operation of a first embodiment of a device in accordance with the invention for indicating whether the part for medical usage has completed a prescribed thermal cycle, wherein a spring made of memory metal is used as a temperature-sensitive element.
Figure 2:
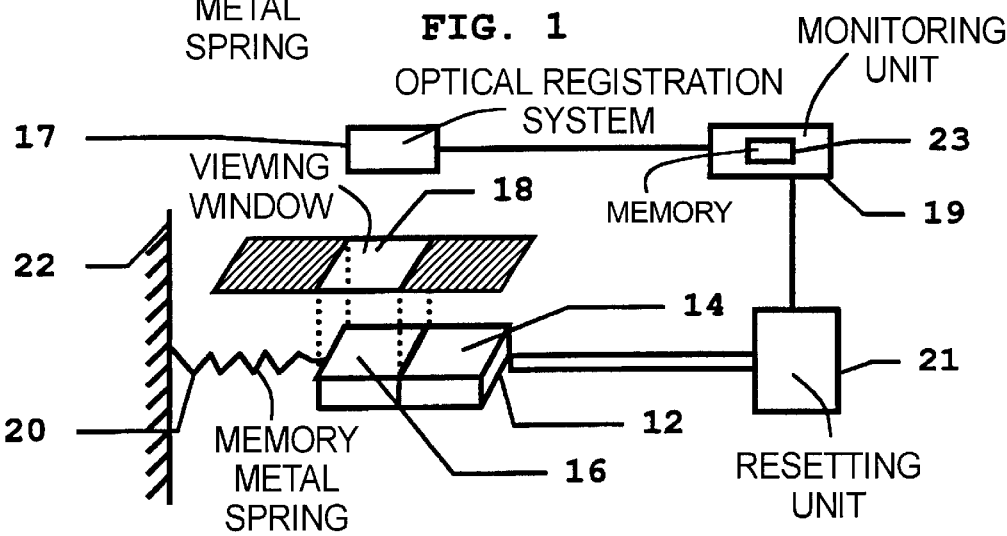
Figure 3:
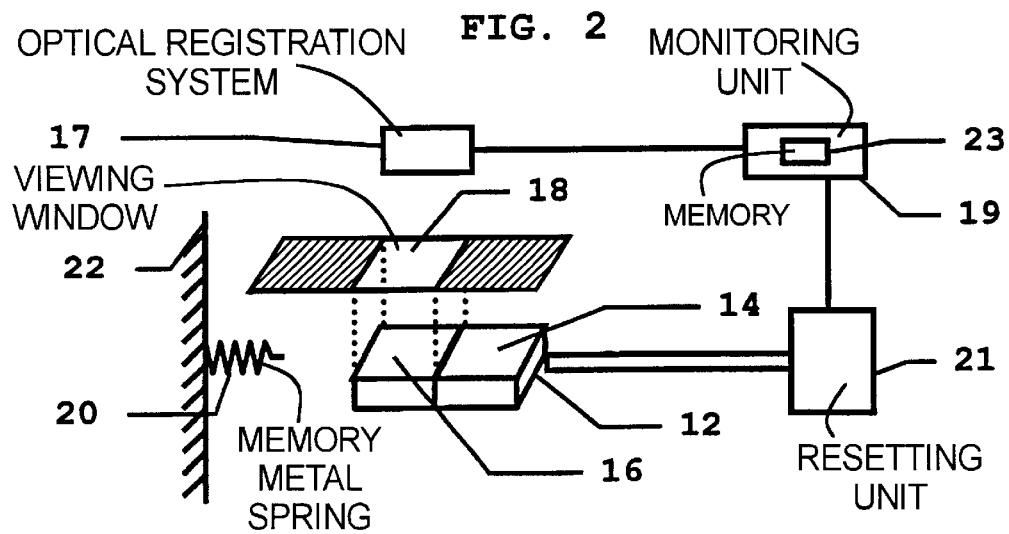

FIGS. 1–3 are schematic depictions showing the functioning of a device for registering a thermal cycle in accordance with the invention. The device has an indicator element in form of a plate 12 with two indication fields 14, 16, e.g. a green field and a red field. The plate 12 can be moved with a memory metal spring 20 which changes shape with the temperature. The first field 14 or the second field 16 is then visible to an operator through a window 18 depending on whether the plate 12 is in a first indication position (showing first field 14) or in a second indication position (showing second field 16)

FIG. 1 shows the "cold" state with the spring 20 retracted and the plate 12 in the first indication position in which the first (red) field 16 is visible through the window 18.

The device pictured in FIGS. 1–3 is designed to be arranged on a part for medical usage. When the part is heated for sterilization purposes, the spring 20 changes shape by elongation as the temperature passes a predetermined threshold value. When the spring 20 presses against a rigid support 22, it shifts the plate 12 to the right in the FIG. (see FIG. 2) until the second (green) field 16 becomes visible through the window 18. This shows the operator that the part in question has been subjected to sufficient sterilization heating and is ready for use. The spring 20 contracts as the part cools (see FIG. 3). The plate 12 can then be reset to the position shown in FIG. 1, i.e. with the first (red) field 14 displayed in the window 18.

Alternately, as also indicated in FIGS. 1–3, an optical system 17 can be used for automatic registration of the position of the plate 12. Instead of using different colors of the fields 14, 16, different reflection characteristics can be used. Registration of the movement of the plate 12 by the optical system 17 is transferred to a monitoring unit 19.

Within the monitoring unit 19 is a memory 23 for accumulative counting of the number of sterilization cycles. This number, as well as indication of the present position of the plate 12, can be displayed to an operator via a screen or other display means (not shown)

The plate 12 can be automatically reset by a resetting unit 21 when the part for medical usage is attached to a mother unit or put to use, causing the plate 12 to be reset. The resetting unit 21 can be controlled from the monitoring unit 19 or in any other suitable manner, such as by a separate pulse magnet, motor or the like.

A bimetallic spring can also be used for shifting the plate 12 instead of the spring 20 made of memory metal.

Figure 4:
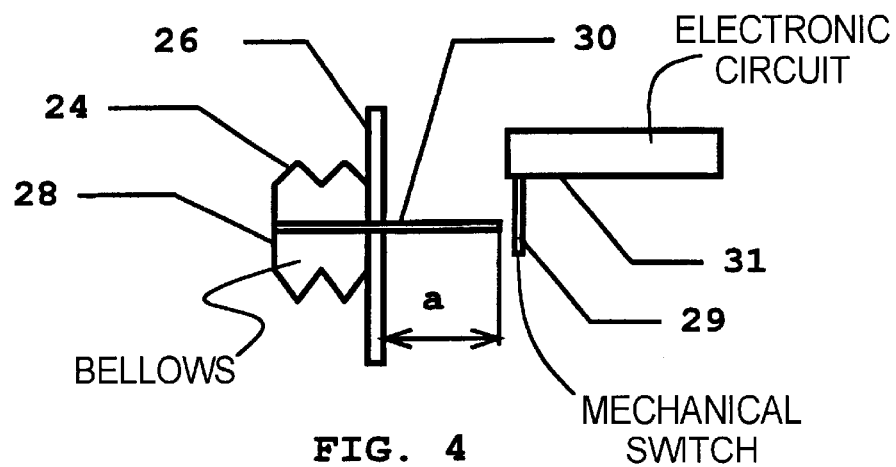
FIGS. 4–5 schematically depict an alternative temperature-and/or pressure-sensitive element in the form of a bellows for use in the inventive device.
Figure 5:
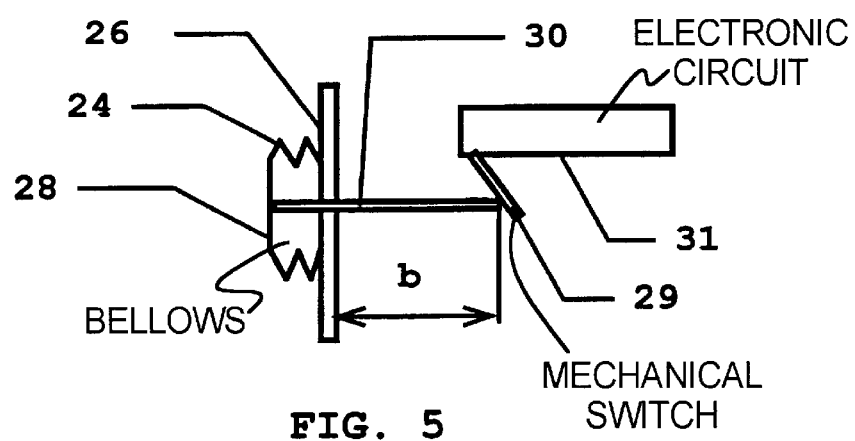

Alternately, a gas-filled hermetically sealed bellows 24 can be used as the temperature-sensitive element and/or pressure-sensitive element for shifting the plate when autoclaving under positive pressure, as shown in FIGS. 4 and 5. One end of the bellows 24 is affixed to a rigid support 26, and its other end 28 is able to move as the volume of the bellows changes. An operating pin 30, which passes through the bellows 24 and through the support 26, is attached to the end 28 to move the indicator plate (not shown in FIGS. 4 and 5) when the bellows 24 is compressed.

When the part for medical usage, equipped with the device according to the invention, is at atmospheric pressure, the bellows assumes the position shown in FIG. 4 and the end of the operating pin 30 is at a distance a from the support 26.

When the medical part with the device according to the invention is autoclaved under positive pressure, the bellows 24 is compressed. The pin 30 will move to project a distance b beyond the support 26, b then being>a (see FIG. 5). The movement will shift the plate in such a way that the second field becomes visible in the inspection window, as shown in FIGS. 1–3 above.

As an alternative, the operating pin 30 by itself can be used as the indicator element. The operating pin 30 can then be arranged to translate its movement into measurable changes in inductance or capacitance, or the indicator element can be arranged so its movement opens and closes an electronic circuit 31 via a mechanical switch 29, as shown in FIGS. 4 and 5.

The embodiments shown in FIGS. 1–5 are intended for attachment to the medical part or component. Information about sterilization or autoclaving is therefore incorporated into the part itself. The part is also able to add the total number of autoclaving cycles as disclosed above.

Figure 20:
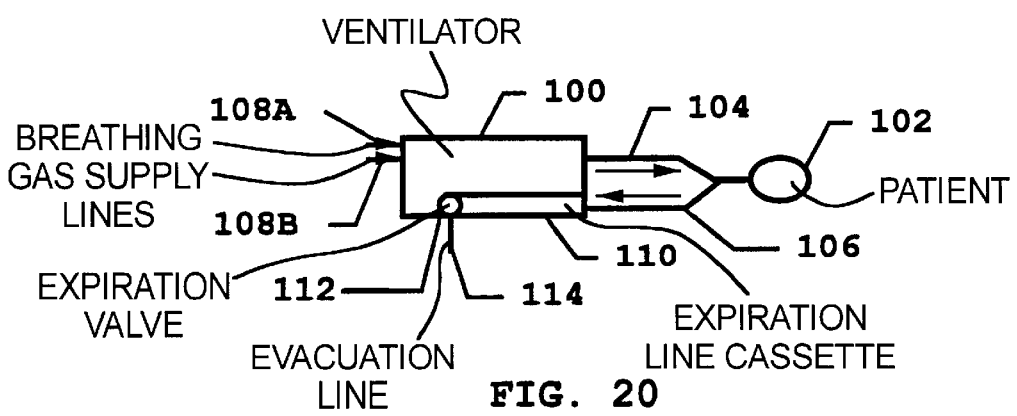
FIG. 20 shows the use of the device according to the invention in a ventilator.

Use of the device in a ventilator 100 is shown in FIG. 20. The ventilator 100 is connected to a patient 102 via an inspiration tube 104 and an expiration tube 106. Breathing gas is connected to the ventilator 100 via a first gas line 108A and a second gas line 108B. The expiration tube 106 leads exhaled gas to an expiration line cassette 110 in the ventilator 100. An expiration valve 112, either placed in the cassette 110 or coupled to it during use, is used to regulate the outflow of gas via evacuation line 114. The expiratory cassette 110 must be autoclaved for each new patient 102. The cassette 110 can withstand only a limited number of autoclaving or sterilization cycles e.g. 100. The cassette 110 is therefore equipped with a device according to the invention. When a device according to any of FIGS. 1–3 is used, resetting of the indicator element can be made the first time the expiration valve 112 opens for a new patient 102.

Figure 6:
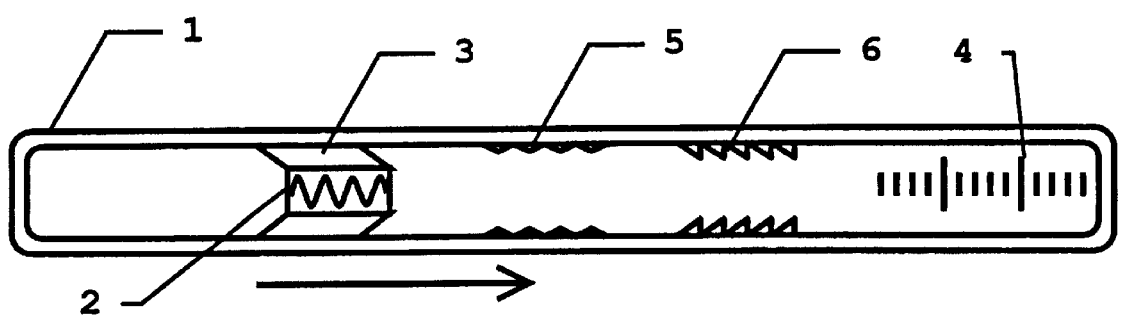
FIG. 6 schematically depicts a first embodiment of a nonvolatile memory for accumulating registration of the number of thermal cycles completed by the part for medical usage in accordance with the invention.

FIG. 6 shows a first embodiment of such a device for accumulatively storing the number of thermal cycles to which a part has been subjected. Here, a temperature-sensitive element and/or pressure-sensitive element is utilized. The element is appropriately made of e.g. memory metal, usually a NiTi alloy which reversibly changes its physical shape at a specific switching temperature $T_1$ that is selectable within wide limits. The change in shape, as well as the mechanical force developed in the shape change, can be made large. The force of this shape change can also be used in the embodiments according to FIGS. 1–3 for shifting the plate 12, as described above.

Figure 7:
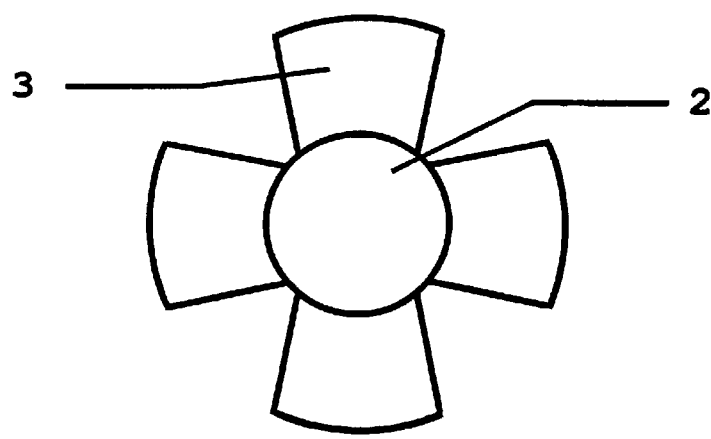
FIGS. 7 and 8 depict in greater detail the moving body shown in FIG. 6 for registering the number of thermal cycles.
Figure 8:
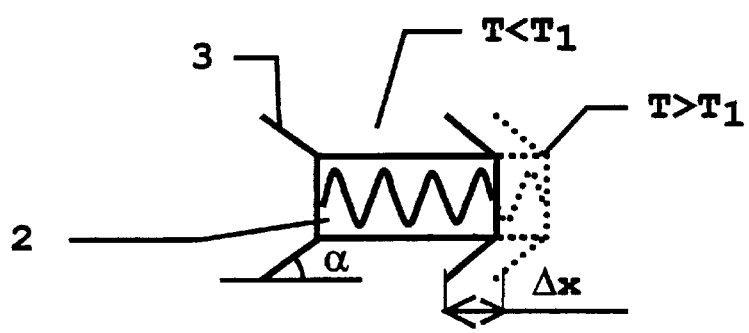

In the embodiment according to FIGS. 6–8, the change in shape can be used for accumulative, one-way, linear movement of an indicator element. The device has a tube 1, preferably made of glass or transparent plastic, which is hermetically sealed at both ends. A moving body 2 is arranged inside the tube 1 and is held relatively firmly in place by two sets of wings or flanges 3, made of thin plastic, rubber or metal, which press against the wall of the tube 1. When the angle α of the wings 3 in relation to the tube's longitudinal axis is appropriately selected, the wings 3 serve as ratchet pawls, preventing the moving body 2 from moving in any direction except to the right in the tube 1.

The moving body 2 is formed by the temperature-sensitive element and/or pressure-sensitive element coupled together with the indicator element and suitably is an element made of memory metal which, when the temperature rises to a switching temperature $T_1$, increases its length by an increment of $\Delta x$ (see FIG. 8). The moving body 2 resumes its original length when the temperature drops below $T_1$. This elongation and subsequent contraction cause the moving body 2 to move the distance $\Delta x$ inside the tube 1. In other words, for each thermal cycle the moving body 2 moves from a first indication position to a second indication position.

The switching temperature $T_1$ and the elongation $\Delta x$ are set with a tempering and deformation procedure at the time the moving body 2 is manufactured. Depending on the accuracy and desired system dynamics, $\Delta x$ can be selected to vary from short distances, i.e. on the order of about 0.01 mm, up to several millimeters. The tube 1 typically can be 5 cm long and about 10 mm in diameter.

Simple reading of the number of completed thermal cycles, in which $T>T_1$, could be by direct reading of the position of the moving body 2, as with a thermometer, when the tube 1 is transparent. Graduations are shown at 4. In order to indicate whether the device has gone through a thermal cycle since the last use, an indicator as shown in FIGS. 1–3 can suitably be combined with the device of FIG. 6.

The interior of the tube 1 can be completely smooth or somewhat roughened, as shown at 5, to increase friction between the wall and wing 3. The tube 1 can also be equipped with serrated notches 6 with a specific pitch, approximately equal to $\Delta x$. This enables the moving body 2 to "advance" only if the expansion of the moving body 2 is greater than or equal to $\Delta x$. This accordingly prevents "advancing" caused by ordinary thermal expansion in cycles in which $T<T_1$. If correct magnitudes are selected for the angle α (see FIG. 8), the correct material is chosen for wings and the tube, a correct angle is selected for the "serrations" etc. the risk of the moving body 2 "advancing" because of temperatures consistently less than the switching temperature $T_1$ is completely eliminated. At the same time, the risk of unintentional movement by the moving body 2 in the "wrong" direction when the device is shaken or for some other reason is completely eliminated.

Since a moving body 2 including a memory metal can develop great force during thermal elongation, friction between the moving body 2 and the wall of the tube 1 can be made relatively large to prevent acceleration forces, jolts, vibration etc. from causing the moving body 2 to move inside the tube 1.

Thus, the advantage of using memory metal in the moving body 2 is that memory metal, at a specific temperature, undergoes a sudden and relatively large change in shape of a completely different magnitude than the change in shape occurring in conventional linear thermal expansion, as noted above. In instances in which the inside wall of the tube 1 is provided with notches 6, a moving body 2 formed by e.g. a bimetallic element can also be used. A bimetallic element produces a large change in shape which, however, is linear as a function of temperature. In this version, the moving body 2 inside a smooth-walled tube 1 would move in every temperature cycle, even if the actual temperature remained consistently below the threshold $T_1$. However, if the interior wall of the tube 1 were provided with notches 6, the bimetallic moving body 2 is devised so its temperature-related linear elongation $\Delta x$ is equal to the pitch of the serration at the temperature threshold $T_1$. The moving body 2 then advances one notch 6 when, and only when, the temperature in the cycle exceeds the threshold $T_1$. The same function is achieved as in the version with a moving body 2 made of a memory metal in a tube 1 with smooth walls.

In instances in which the interior walls of the tube 1 are devised with notches 6 at specific distances from one another, the moving body 2 can be made of other materials, such as polymers, gases, other metals etc., whose thermal expansion is employed to produce the movement of the moving body 2.

Figures 9A, 9B:
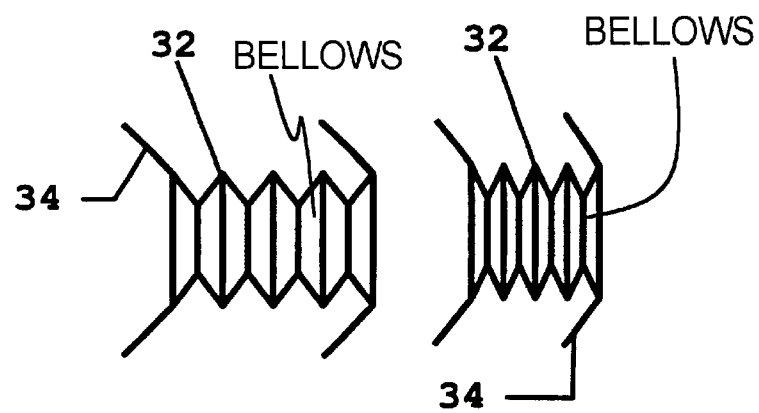
FIGS. 9A and 9B show an alternative embodiment of the moving body of FIG. 6 in the form of a hermetically sealed, gas-filled metal bellows.

A pressure-sensitive element in the form of a hermetically sealed gas-filled or air-filled metal bellows 32 can also be used as a moving body, as shown in FIGS. 9A and 9B. Pressure inside the bellows 32 can amount to e.g. 1 bar absolute. During heating, the gas expands, and the bellows 32 elongates by the distance $\Delta x$, (which analogously applies to this embodiment) depending on the stiffness of the bellows 32 and the temperature rise. The bellows is shown in the "cold" state in FIG. 9B and in the elongated state in FIG. 9A.

In autoclaving under positive pressure, the moving body is shifted according to another principle. The autoclaving is performed in a kind of "pressure cooker" in which the pressure is 3.6 bar at a temperature of 140° C. According to the general gas law, PV/T=constant, in which P designates pressure, V Volume and T temperature, the bellows 32 will be compressed to about 0.38 times its original length if the stiffness of the bellows 32 is disregarded. The compressive force is considerable here. When the bellows has a diameter of 5 mm, the force will initially be about 5 N. When an appropriate stiffness is selected for the bellows 32, a desired change in length in an autoclaving cycle can be obtained. Also see FIGS. 4 and 5.

The bellows 32 is equipped with two sets of ratchet pawl wings or flanges 34, as also noted in the description of FIGS. 6–8.

Embodiments for direct reading of the number of completed thermal cycles on a graduated scale were described above. The device according to the invention, however, can also be devised for electronic reading and display of the number of cycles in the mother unit, e.g. a ventilator. Since the device according to the invention must be simple and inexpensive and is also exposed to moisture, high temperatures etc., complex parts, electronics, batteries etc. preferably should be housed in the mother apparatus to the greatest possible extent. Several versions in which this function is realized are described below.

Figure 10:
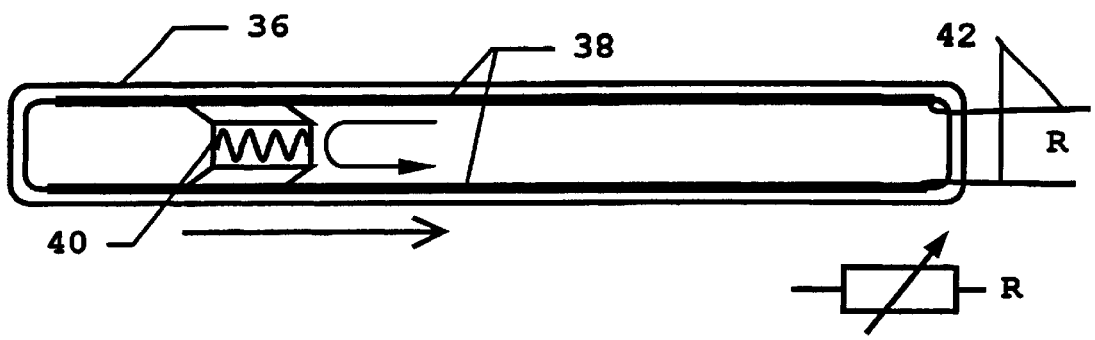
FIG. 10 illustrates another version of the embodiment in FIG. 6, wherein movement of the moving body causes a change in the resistance of an electrical conductive pathway allowing electrical measurement of the moving body's position.

FIG. 10 shows a tube of the kind depicted in FIG. 6 with two conductive pathways 38 made of a resistive material, resistor wire etc. deposited on the interior walls of the tube. These conductive pathways 38 are short-circuited by the moving body 40. This means that electrical resistance R between the wires 42 decreases the farther the body 40 advances to the right in the tube 36. The position of the body 40, and accordingly the number of completed thermal cycles, therefore can be determined by measuring the resistance R.

Figure 11:
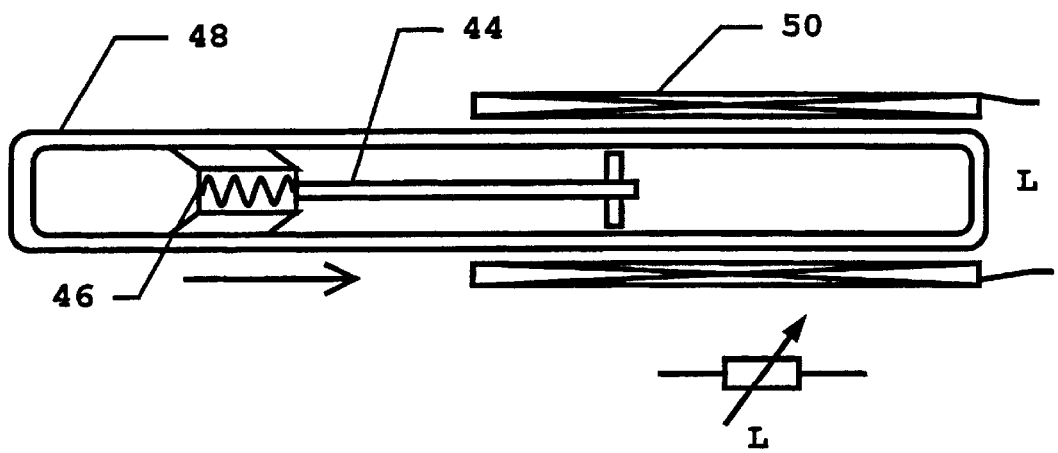
FIGS. 11 and 12 respectively show two other alternative embodiments in which the position of the moving body can be determined by measuring electrical inductance.

FIG. 11 shows an alternative in which a rod 44 made of ferromagnetic, unmagnetized material is connected to the moving body 46. When the body 46 moves to the right in the tube 48, the rod 44 is thrust into a coil 50 that is wound around the exterior of the tube 48 along about half the length of the tube. Inductance L increases as the rod is inserted into the coil 50. The position of the body 46 in the tube 48 can therefore be determined by measuring inductance Alternately, a rod made of non-magnetic conductive material can be used, inductance then decreasing as the rod is inserted into the coil, i.e. field constriction.

Figure 12:
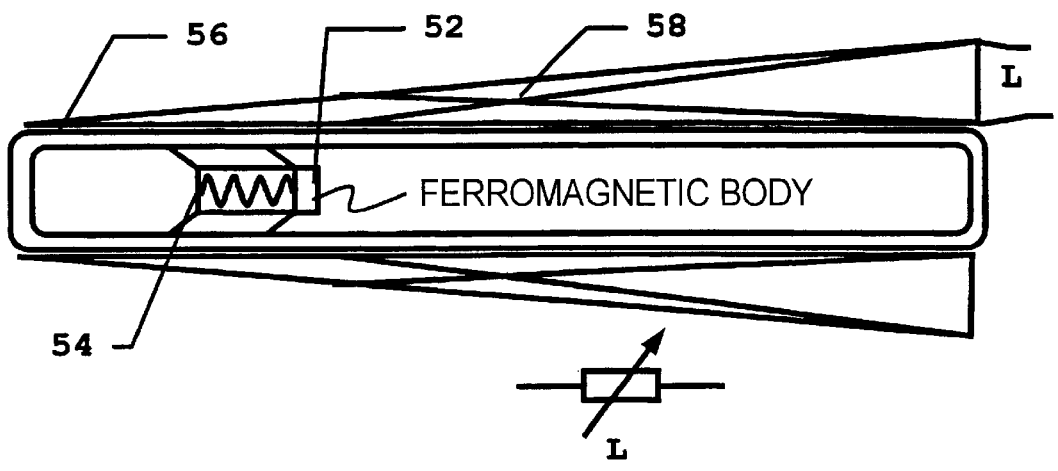

FIG. 12 shows an additional embodiment in which a small ferromagnetic, unmagnetized body 52 is arranged on the moving body 54. The tube 56 is enclosed in a coil 58 whose turns increase linearly per unit of distance to the right in FIG. 12. The inductance of the coil 58 will also increase in this instance when the moving body 54, and accordingly the ferromagnetic body 52, advances to the right in the tube 56. This makes it possible to determine the position of the moving body 54 by measuring inductance L.

The coils in the embodiments shown in FIGS. 11 and 12 do not need to be affixed to the tube but can be in the mother apparatus so the tube is automatically inserted into the coils when the part for medical usage is placed in the mother apparatus.

In an analogous fashion, varying capacitance can be achieved in determining the position of the moving body in the tube. Thus, the tube can be provided with a conductive coating on its interior or exterior. The coating does not cover the entire surface but has a coverage area which decreases from one end of the tube to the other. The coverage area can decrease e.g. conically so the coated area per unit of length declines linearly along the length of the tube. Capacitance between the outer capacitor plate accordingly formed and the moving body, or an appliance connected to the moving body, decreases linearly when the body moves, i.e. the position of the body can be determined by measuring the varying capacitance.

Figure 13:
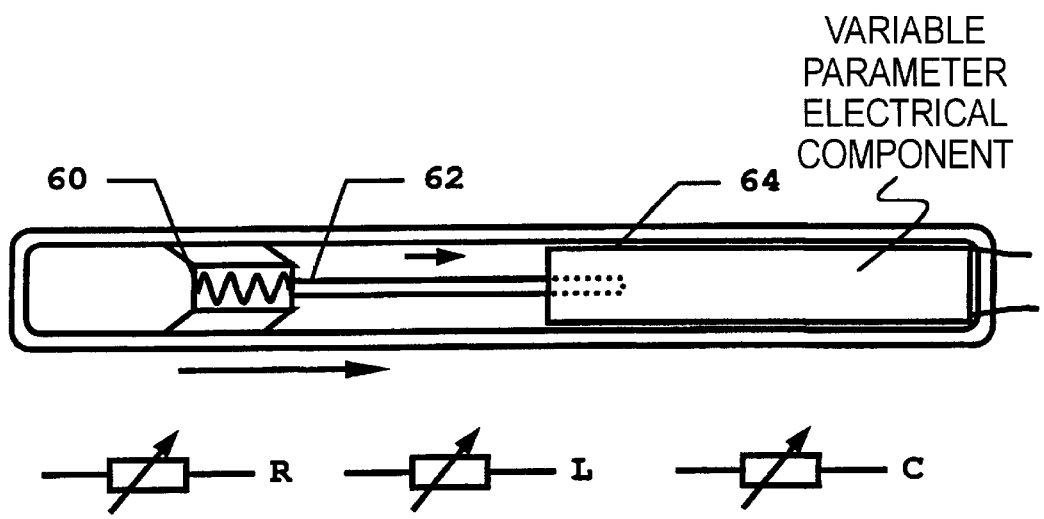
FIG. 13 is a more general illustration of the principle for determining the position of the moving body in a device according to the invention wherein movement of the moving body alters an electrical component with variable resistance, inductance or capacitance or some combination thereof, allowing the moving body's position to be determined by measurement of the these electrical parameters.

FIG. 13 is a general illustration of the way the moving body 60 acts, by means of a moving shaft 62, on an electrical component 64 with variable resistance, inductance or capacitance or a combination of these parameters. Here, commercially available standard components can be used advantageously.

For all embodiments of FIGS. 11–13 a monitoring unit similar to the one shown in FIGS. 1–3 can be utilized for storing and displaying accumulated number of thermal cycles, as well as identifying whether the device has passed a thermal cycle after the most recent usage (and before the next usage)

Figure 14:
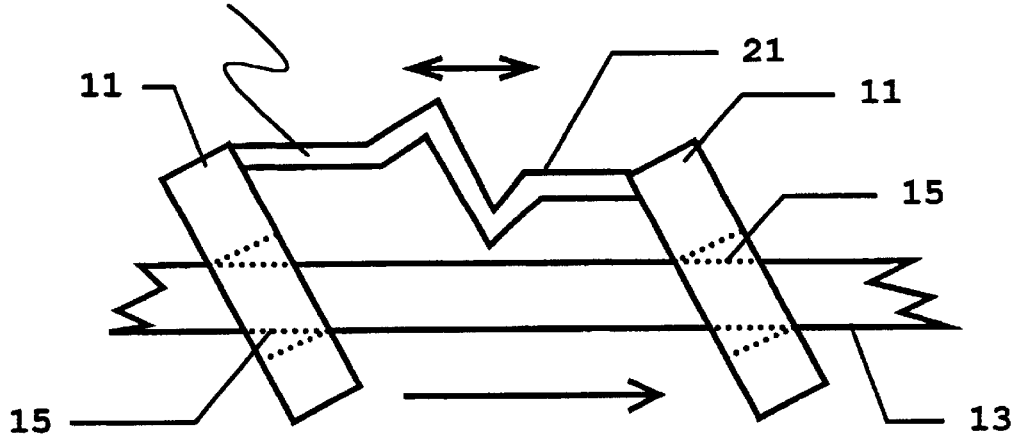
FIG. 14 shows another alternative embodiment of the moving body which advances a specific distance for every thermal cycle completed by the part for medical usage.

FIG. 14 shows an alternative version of the moving body. Two identical discs 11 are mounted on a rod 13 through a hole 15 in the discs. The diameter of the rod 13 is slightly less than the diameter of the holes 15. The discs are interconnected by a temperature-sensitive element 21, suitably made of memory metal, and the element is pretensioned so the discs 11 press against the rod 12 in the normal position, as shown in FIG. 14.

When the length of the temperature-sensitive element 21 increases when the temperature T is greater than the switching temperature $T_1$ during the thermal cycle, the right disc 11 will shift to the right. When the temperature subsequently drops, the left disc 11 will follow, causing the entire body to shift to the right on the rod 13. Movement to the left in the embodiment of FIG. 14 is prevented by friction.

Movement of the moving body 11, 21 can also be used to add the total number of thermal cycles to which the medical part with the device according to the invention has been subjected. A number of mechanical switches, similar to the one shown in FIGS. 4–5 can be arranged so one switch at a time is effected at each thermal cycle, thus indicating that a thermal cycle has passed before the next usage of the device.

Figure 15:
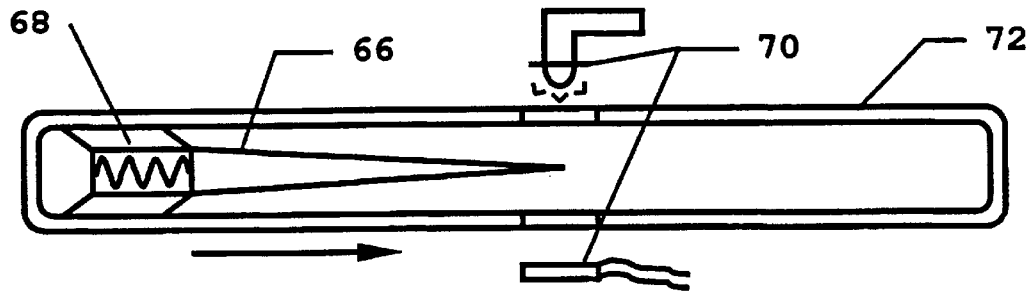
FIG. 15 shows another alternative embodiment for registering the position of the moving body and, accordingly, for determining the number of thermal cycles, using an optical transmission path.

FIG. 15 shows an additional embodiment of the device according to the invention. Here, a conical body 66 is attached to one end of the moving body 68. An optical transmitter/receiver system 70, which changes its electrical output dependent on the amount of light falling on the receiver (receptor) thereof, is arranged to register light transmitted across the tube 72 when the conical body 66 is gradually introduced into the light path as the moving body 68 advances to the right in the tube 72. The receptor 70 can be mounted on the tube 72 or located in the mother apparatus, enabling it to measure light transmitted across the tube 72 when the medical part with the device according to the invention is mounted on the mother apparatus.

FIGS. 16–19 show two additional embodiments of the device according to the invention. They utilize helical movement, instead of linear movement, for totaling the number of thermal cycles.

Figure 16:
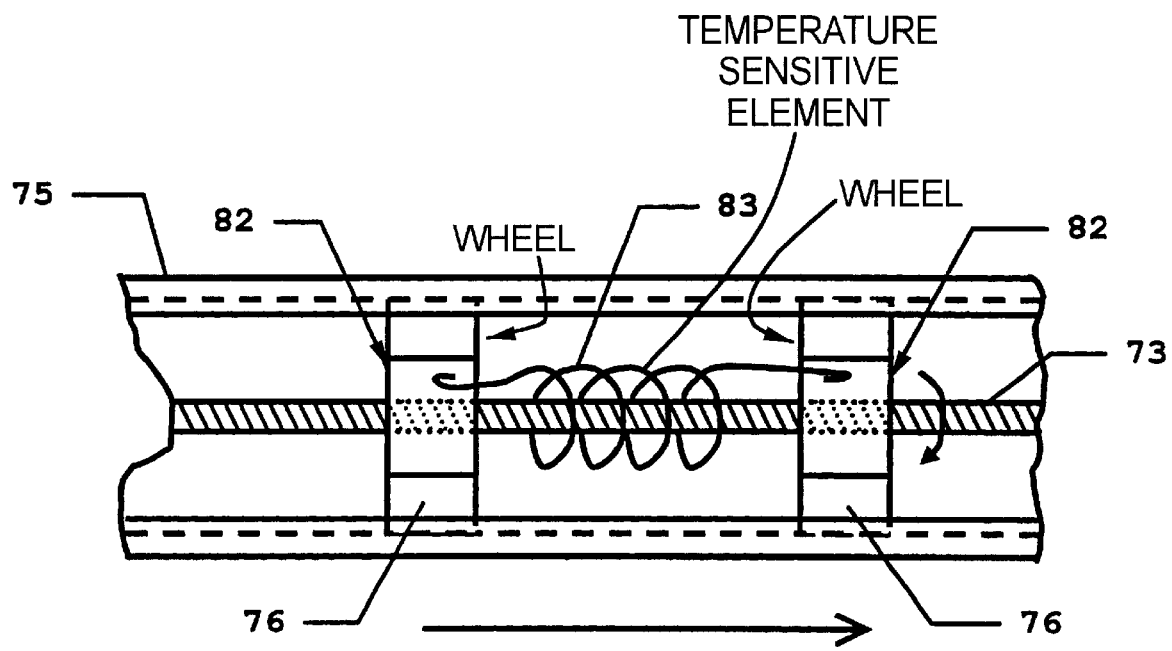
FIG. 16 shows another embodiment of the moving body, which advances a specific distance for each thermal cycle.

The embodiment shown in FIG. 16 has two small, identical threaded wheels 82 on a finely threaded rod 73 inside a tube 75 which can be transparent or opaque. The wheels 82 are equipped with a number of small, flexible wings 76 which press against the wall of the tube 75.

Figure 17:
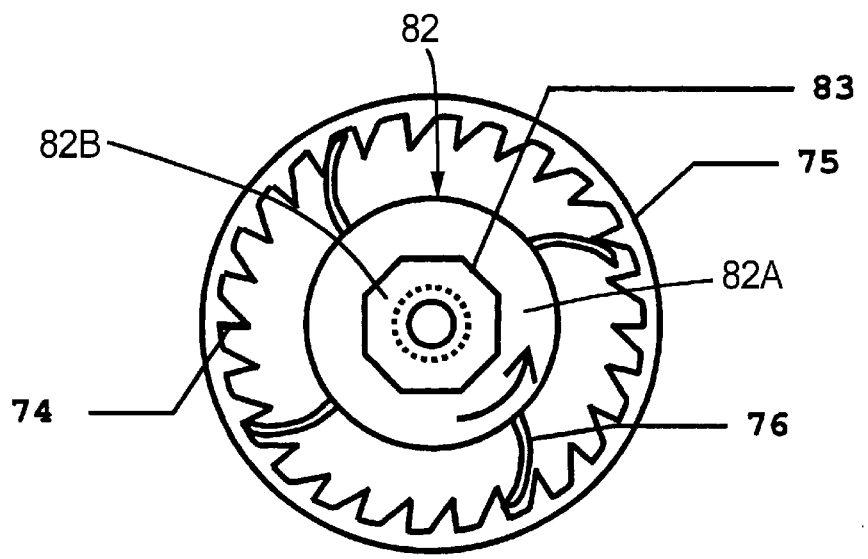
FIGS. 17 and 18 respectively show two versions of the embodiment in FIG. 16 in cross-section across the tube in which the moving body is arranged.

The wheels 82 can be made of e.g. a polymer material, can have a polymer rim 82A pressed-on to a standard metal nut 82B, as shown in FIG. 17.

The interior walls of the tube 75 can be completely smooth. The wings 76 then form an angle with the tube wall, creating a ratchet effect, or can be provided with serrations 74.

The wheels 82 are connected to a temperature-sensitive element 83, suitably made of memory metal or being a bimetallic element, as described above for other embodiments. When the switching temperature T1 is exceeded, the shape of the element 83 changes, causing the moving body formed by the wheels 82 to be threaded in steps so as to advance along the threaded rod 73. Great accuracy can be obtained and a large number of cycles accommodated with a limited length of tubing by suitable selection of the pitch of the thread, the shape of the temperature-sensitive element 84, the number of wings 76 and their placement in relation to one another and, where applicable, the number of serrated notches 74.

Other types of ratchet wheel functions can obviously be used. Some friction between the wheels 82 and the threaded rod 73 is permissible, even desirable, to prevent wheel rotation caused by vibration etc. This is possible, since memory metal can develop considerable force when changing shape.

The type of device according to the invention is more reliable, more accurate, and less sensitive to jolts, acceleration and vibration and is able, for a given size, to register a much larger number of thermal cycles than the linear version.

In theory, "resolution" in the version with a smooth tubular wall is infinitely high but is finite in practice due to friction, the resilience of the wings 76 etc. If the change in shape is very small, the body will not move but remain in place and quiver, as noted above.

FIG. 17 shows about 30 serrated notches around the circumference of the tube. This would yield a resolution of 360/30=12°.

Figure 18:
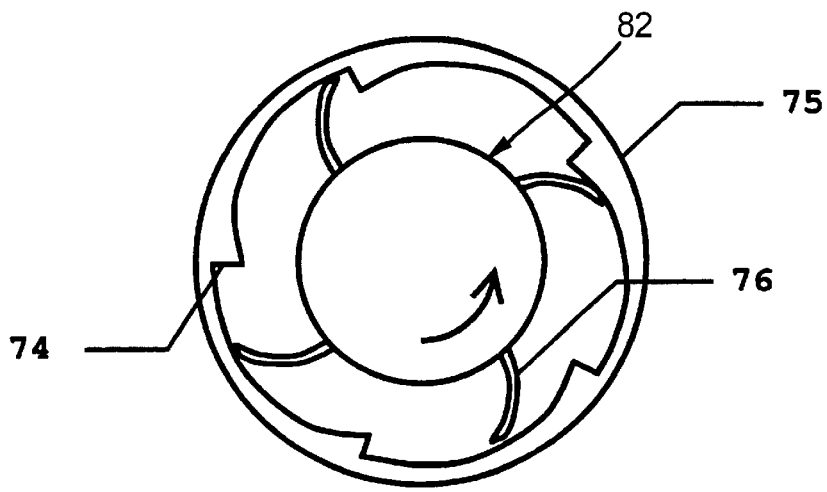

FIG. 18 shows how a resolution of 18°, i.e. 20 temperature cycles for each wheel revolution, can be achieved with four ratchet wings 76 and only five serrated notches. Generally speaking, if the number of wings is k and the number of notches n×k+1, where n is an integer 1,2,3 . . . , the increment (360°/nk+1)/k is obtained for each meshing by the wings. For example, 4 wings result in, i.e. k=4 and n=5, i.e. a total of 4×5+1–21 notches, an increment of 4.3°. This corresponds to 84 temperature cycles per revolution on the threaded rod 73. High resolution thus can be obtained with just a few wings and notches, thereby facilitating fabrication.

Figure 19:
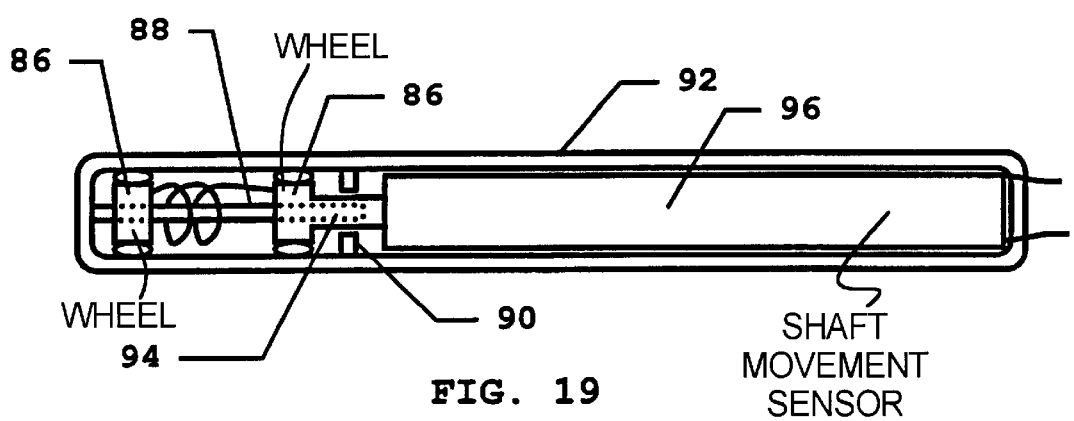
FIG. 19 shows another embodiment of the device according to the invention for registering the number of thermal cycles with a moving body whose movement is translated into a measurable electrical parameter.

FIG. 19 shows an additional embodiment in which the wheels 86 are not threaded, and the shaft 88 is a smooth rod. The wheels 86 rotate a specific number of degrees for every registered temperature cycle but are not translated, i.e. the rotational position designates the accumulated number of thermal cycles.

The stop 90 is devised so the wheels 86 are always kept in the left part of the tube 92. The rotary movement is generated in some way analogous to the movement in the embodiment according to FIG. 16.

The rotary movement is mediated by a shaft 94 from the right wheel 86 to an electrical sensor 96 from which accumulated rotation can be read.

The sensor 96 is a commercially available product and can be a type in which e.g. a piece of iron is moved inside a coil by the movement of the shaft 94, causing a change in inductance, or the shaft 94 can rotate a potentiometer shaft, move a inside a light transmission path according to FIG. 15, rotate a variable capacitor or rotate a variable inductor.

Combinations among the shown embodiments, other than those explicitly mentioned, are also possible, in particular combinations involving registration and display of information.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for repeated registration of a number of thermal cycles to which a part for medical usage is subjected, comprising:
   at least one temperature-responsive element selected from the group of elements consisting of temperature-sensitive elements and pressure-sensitive elements associated with a part for which a number of thermal cycles to which said part has been subjected is to be identified;

said temperature-responsive element having a physical shape which reversibly changes dependent on at least one of temperature and pressure, with variations in pressure always occurring with temperature changes;

an indicator element which is normally disposed in a first indication position and which is disposed to interact with said at least one temperature-responsive element so as to move to a second indication position when the change in physical shape of said temperature-responsive element exceeds a predetermined threshold value;

a registration unit communicating with said indicator element to register movement of said indicator element from said first indication position to said second indication position as an identification of said part undergoing a thermal cycle; and a resetting unit in mechanical communication with said indicator element for automatically resetting said indicator element to said first indication position upon an occurrence of a predetermined condition.

2. A device as claimed in claim 1 wherein said registration unit comprises a memory for accumulatively storing a total number of movements of said indicator element from said first indication position to said second indication position.

3. A device as claimed in claim 1 wherein said part for medical use is a component of a ventilator, and wherein said ventilator comprises an expiration line cassette containing said part, and an expiratory valve in communication with said expiration line cassette, and wherein said resetting unit comprises a resetting unit which resets said indicator element to said first indication position upon a first opening of said expiratory valve.

4. A device as claimed in claim 1 wherein said temperature-responsive element is comprised of memory metal.

5. A device as claimed in claim 1 wherein said temperature-responsive element is a bimetallic element.

6. A device for repeated registration of a number of thermal cycles to which a part for medical usage is subjected, comprising:

at least one temperature-responsive element selected from the group of elements consisting of temperature-sensitive elements and pressure-sensitive elements associated with a part for which a number of thermal cycles to which said part has been subjected is to be identified;

said temperature-responsive element having a physical shape which reversibly changes dependent on at least one of temperature and pressure, with variations in pressure always occurring with temperature changes;

an indicator element which is normally disposed in a first indication position and which is disposed to interact with said at least one temperature-responsive element so as to move to a second indication position when the change in physical shape of said temperature-responsive element exceeds a predetermined threshold value; and, said indicator element performing an accumulating one-way movement in a single direction in a plurality of successive thermal cycles, with said second indication position in a succeeding thermal cycle corresponding to the first indication position in a thermal cycle preceding said succeeding thermal cycle; and a registration unit communicating with said indicator element to register movement of said indicator element from said first indication position to said second indication position as an identification of said part undergoing a thermal cycle.

7. A device as claimed in claim 6 wherein said registration unit comprises a tube, and wherein said temperature-responsive element and said indicator element are coupled together to form a moving body disposed inside said tube, said moving body moving incrementally in said single direction inside said tube during respective thermal cycles in said successive thermal cycles.

8. A device as claimed in claim 7 wherein said tube has an interior surface with a plurality of notches respectively spaced from each other at predetermined distances along a length of said tube, and wherein said moving body comprises a set of radially-projecting flanges which engage said notches to form a ratchet pawl allowing said moving body to incrementally move only if a change in a length of said moving body during a thermal cycle exceeds said distance between two successive notches in said plurality of notches.

9. A device as claimed in claim 8 wherein said moving body comprises a threaded rod disposed inside said tube and two threaded wheels threadably engaging said threaded rod, each of said wheels carrying said flanges thereon, said wheels being spaced apart from each other on said rod and said threaded wheels rotating in only one direction on said threaded rod and advancing along said threaded rod in said increments each time a thermal cycle exceeds said threshold.

10. A device as claimed in claim 7 wherein said moving body comprises a hermetically sealed, gas-filled bellows which is elongated in said direction by expansion of the gas when temperature increases.

11. A device as claimed in claim 7 wherein said thermal cycle includes autoclaving said part under positive pressure, and wherein said moving body comprises a hermetically sealed bellows which is compressed by said positive pressure, and which subsequently elongates in said direction after autoclaving, causing incremental movement of said bellows in said direction.

12. A device as claimed in claim 6 wherein said registration unit comprises a memory for accumulatively storing a total number of movements of said indicator element from said first indication position to said second indication position.

13. A device as claimed in claim 6 wherein said temperature-responsive element is comprised of memory metal.

14. A device as claimed in claim 6 wherein said temperature-responsive element is a bimetallic element.

15. A device for repeated registration of a number of thermal cycles to which a part for medical usage is subjected, comprising:

at least one temperature-responsive element selected from the group of elements consisting of temperature-sensitive and pressure-sensitive elements associated with a part for which a number of thermal cycles to which said part has been subjected is to be identified;

said temperature-responsive element having a physical shape which reversibly changes dependent on at least one of temperature and pressure, with variations in pressure always occurring with temperature changes;

an indicator element which is normally disposed in a first indication position and which is disposed to interact with said at least one temperature-responsive element so as to move to a second indication position when the change in physical shape of said temperature-responsive element exceeds a predetermined threshold value;

a registration unit communicating with said indicator element to register movement of said indicator element from said first indication position to said second indication position as an identification of said part undergoing a thermal cycle; and said registration unit comprising a rod and said indicator element comprising two disks, each having a hole therein, disposed spaced from each other on said rod with said rod extending through said holes and allowing said disks to slide along said rod, and said temperature-responsive element mechanically interconnecting said disks and normally pressing said disks against said rod in a locked position and causing said disks to advance in a single direction along said rod by elongation of said temperature-responsive element when said threshold value is exceeded.

16. A device as claimed in claim 15 wherein said registration unit comprises a memory for accumulatively storing a total number of movements of said indicator element from said first indication position to said second indication position.

17. A device as claimed in claim 15 wherein said temperature-responsive element is comprised of memory metal.

18. A device as claimed in claim 15 wherein said temperature-responsive element is a bimetallic element.

19. A device for repeated registration of a number of thermal cycles to which a part for medical usage is subjected, comprising:

at least one temperature-responsive element selected from the group of elements consisting of temperature-sensitive elements and pressure-sensitive elements associated with a part for which a number of thermal cycles to which said part has been subjected is to be identified:

said temperature-responsive element having a physical shape which reversibly changes dependent on at least one of temperature and pressure, with variations in pressure always occurring with temperature changes;

an indicator element which is normally disposed in a first indication position and which is disposed to interact with said at least one temperature-responsive element so as to move to a second indication position when the change in physical shape of said temperature-responsive element exceeds a predetermined threshold value;

a registration unit communicating with said indicator element to register movement of said indicator element from said first indication position to said second indication position as an identification of said part undergoing a thermal cycle; and said registration unit including a tube and said indicator element and said temperature-responsive element being coupled together to form a moving body which incrementally moves in said tube with an incremental movement caused by each thermal cycle, and said registration unit comprising an electrical circuit, having a variable electrical parameter, which changes dependent on said incremental movement of said moving body, said electrical parameter being selected from the group of electrical parameters consisting of resistance, inductance and capacitance.

20. A device as claimed in claim 19 wherein said parameter comprises resistance, and wherein said electrical circuit comprises two longitudinal conductive pathways disposed in an interior of said tube, said pathways being short-circuited by said moving body.

21. A device as claimed in claim 19 wherein said electrical parameter comprises inductance and wherein said electrical circuit includes a coil wound around at least a portion of said tube, and wherein said moving body comprises an appliance attached thereto consisting of an axially-oriented rod composed of magnetic material which is successively inserted into said coil as said moving body incrementally moves, said rod causing an incremental increase in said inductance as a result of each thermal cycle.

22. A device as claimed in claim 19 wherein said electrical parameter comprises inductance and wherein said electrical circuit includes a coil wound around at least a portion of said tube, and wherein said moving body comprises an appliance attached thereto consisting of an axially-oriented rod composed of non-magnetic material which is successively inserted into said coil as said moving body incrementally moves, said rod causing an incremental decrease in said inductance as a result of each thermal cycle.

23. A device as claimed in claim 19 wherein said electrical component comprises a coil wound around at least a part of said tube with coil turns that increase linearly per unit length from a first end of said coil to a second end of said coil, and wherein said moving body comprises an appliance consisting of unmagnetized, ferromagnetic material which is inserted an incremental distance into said coil as said moving body incrementally moves for each thermal cycle.

24. A device as claimed in claim 19 wherein said electrical parameter comprises capacitance, and wherein said electrical circuit comprises a conductive coating covering at least a portion of an interior and an exterior of said tube with a degree of surface-area coverage varying from a first end of said tube to a second end of said tube, and wherein said incremental movement of said moving body causes incremental capacitance changes between said coating and said moving body as said moving body incrementally moves in said tube during a thermal cycle.

25. A device as claimed in claim 19 wherein said registration unit comprises a memory for accumulatively storing a total number of movements of said indicator element from said first indication position to said second indication position.

26. A device as claimed in claim 19 wherein said temperature-responsive element is comprised of memory metal.

27. A device as claimed in claim 19 wherein said temperature-responsive element is a bimetallic element.

28. A device for repeated registration of a number of thermal cycles to which a part for medical usage is subjected, comprising:

at least one temperature-responsive element selected from the group of elements consisting of temperature-sensitive elements and pressure-sensitive elements associated with a part for which a number of thermal cycles to which said part has been subjected is to be identified;

said temperature-responsive element having a physical shape which reversibly changes dependent on at least one of temperature and pressure, with variations in pressure always occurring with temperature changes;

an indicator element which is normally disposed in a first indication position and which is disposed to interact with said at least one temperature-responsive element so as to move to a second indication position when the change in physical shape of said temperature-responsive element exceeds a predetermined threshold value;

a registration unit communicating with said indicator element to register movement of said indicator element from said first indication position to said second indication position as an identification of said part undergoing a thermal cycle; and said temperature-responsive element and said indicator element being coupled together to form a moving body, and said registration unit comprising a tube in which said moving body is disposed, said moving body having a tapering appliance attached thereto which moves along a length of said tube together with said moving body, and said registration unit further comprising a light transmitter which transmits light through said tube in a direction substantially perpendicular to said length and a light receiver which receives said light, said appliance increasingly blocking light between said transmitter and said receiver as said moving body incrementally moves in said tube during a thermal cycle.

29. A device as claimed in claim 28 wherein said registration unit comprises a memory for accumulatively storing a total number of movements of said indicator element from said first indication position to said second indication position.

30. A device as claimed in claim 28 wherein said temperature-responsive element is comprised of memory metal.

31. A device as claimed in claim 28 wherein said temperature-responsive element is a bimetallic element.

32. A device for repeated registration of a number of thermal cycles to which a part for medical usage is subjected, comprising:

at least one temperature-responsive element selected from the group of elements consisting of temperature-sensitive elements and pressure-sensitive elements associated with a part for which a number of thermal cycles to which said part has been subjected is to be identified;

said temperature-responsive element having a physical shape which reversibly changes dependent on at least one of temperature and pressure, with variations in pressure always occurring with temperature chances;

an indicator element which is normally disposed in a first indication position and which is disposed to interact with said at least one temperature-responsive element so as to move to a second indication position when the change in physical shape of said temperature-responsive element exceeds a predetermined threshold value, said indicator element comprising two wheels, each having an opening therein, and a rod extending through the respective openings in said two wheels, said wheels rotating in only one direction around said rod and being interconnected to each other by said temperature-responsive element, said wheels incrementally rotating in steps of a predetermined angle in said direction during each thermal cycle; and a registration unit communicating with said indicator element to register movement of said indicator element from said first indication position to said second indication position as an identification of said part undergoing a thermal cycle.

33. A device as claimed in claim 32 wherein said registration unit comprises a memory for accumulatively storing a total number of movements of said indicator element from said first indication position to said second indication position.

34. A device as claimed in claim 32 wherein said temperature-responsive element is comprised of memory metal.

35. A device as claimed in claim 32 wherein said temperature-responsive element is a bimetallic element.

* * * * *